United States Patent
Plate et al.

(10) Patent No.: US 6,579,864 B1
(45) Date of Patent: Jun. 17, 2003

(54) 3-METHYLENE STEROID DERIVATIVES

(75) Inventors: Ralf Plate, Oss (NL); Wilhelmina Maria Bagchus, Arnhem (NL)

(73) Assignee: Akzo Nobel NV, Arnhem (NL)

( * ) Notice: Subject to any disclaimer, the term of this patent is extended or adjusted under 35 U.S.C. 154(b) by 0 days.

(21) Appl. No.: 10/148,247

(22) PCT Filed: Nov. 23, 2000

(86) PCT No.: PCT/EP00/11787

§ 371 (c)(1),
(2), (4) Date: May 29, 2002

(87) PCT Pub. No.: WO01/40253

PCT Pub. Date: Jun. 7, 2001

(30) Foreign Application Priority Data

Nov. 29, 1999 (EP) .............................. 99204000

(51) Int. Cl.$^7$ .......................... A61K 31/56; C07J 41/00; C07J 13/00

(52) U.S. Cl. .................. 514/177; 514/178; 514/182; 514/169; 552/515; 552/516; 552/519; 552/526; 552/530; 552/533

(58) Field of Search ................... 514/177, 178, 514/182; 552/519, 526, 530, 533

(56) References Cited

U.S. PATENT DOCUMENTS

| 3,213,117 A | * 10/1965 | Cross ..................... 260/397.4 |
| 3,301,880 A | 1/1967 | Van Vliet et al. ........ 260/397.5 |

FOREIGN PATENT DOCUMENTS

| EP | 157 739 A | 10/1985 |
| EP | 389 035 A | 9/1990 |
| GB | 2 175 905 A | 12/1986 |

OTHER PUBLICATIONS

Faustini et al. (DN 106:84942, HCAPLUS, abstract of DE 3617883).*
DN 69:36356, HCAPLUS, abstract of NL 6604084.*
Chemical Abstracts, vol. 104, No. 11, Mar. 17, 1986, Columbus, Ohio, US; abstract No. 82238, Verheul, H.A.M. et al: "Effects of tibolone, lynestrenol, ethylestrenol, and desogestrel on autoimmune disorders in NZB/W mice", abstract; example 13, Clin. Immunol. Immunopathol. (1986), 38(2), 198–208.

* cited by examiner

Primary Examiner—Sabiha Qazi
(74) Attorney, Agent, or Firm—Mark W. Milstead

(57) ABSTRACT

The invention concerns a 3-methylene steroid derivative having general formula (1) wherein $R^1$ is H or together with $R^3$ forms a β-epoxide or $R^1$ is absent if there is a 5–10 or 4–5 double bond; $R^2$ is ($C_1$–$C_5$) alkyl or $CF_3$; $R^3$ is βH, β$CH_3$ or together with $R^1$ forms a β-epoxide or $R^3$ is absent if there is a 5–10 double bond; $R^4$ is H, lower alkyl; Y is [H, H], [OH, H], =O, [OH, lower alkyl], [OH, (C2–C5)alkenyl], [OH, ($C_2$–$C_5$)alkynyl] or ($C_1$–$C_6$) alkylidene, whereby said alkyl, alkenyl, alkynyl and alkylidene is optionally halogenated; =$NOR^5$, whereby $R^5$ is H, lower alkyl; dotted lines represent an optional double bond, or prodrugs thereof for the treatment of arthritic diseases and/or autoimmune diseases.

(1)

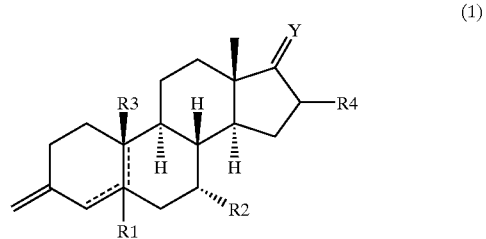

5 Claims, No Drawings

3-METHYLENE STEROID DERIVATIVES

This application is the 35 U.S.C. §371 filing of PCT/EP00/11787, filed Nov. 23, 2000.

FIELD OF THE INVENTION

The invention relates to new 3-methylene steroid derivatives with therapeutic effects and to the preparation of pharmaceutical preparations comprising a 3-alkylidene steroid.

BACKGROUND OF THE INVENTION

Steroids with methylene substituents at the 3 position of the steroid skeleton and 1–2 or 4–5 double bonds are known and claimed to be useful for therapeutic use (BE 696,235 and BE 654,772, respectively). The presumed medical indication is due to anabolic, estrogenic and progestogenic actions. None of these compounds has lived up to the expectations for such use and there was no expectation for utility as medicines in other areas, although many diseases still remain unsatisfactorily treated with presently available drugs. Notably, diseases of the immune system, such as rheumatoid arthritis and autoimmune diseases are in need for better drugs. Corticosteroidal agents are of some use for the treatment of these diseases, but improvements, both with respect to efficacy and number or severity of side effects, are needed.

DETAILED DESCRIPTION OF THE INVENTION

This invention provides for 3-methylene steroid derivatives and prodrugs thereof, which steroid derivatives have the general formula 1

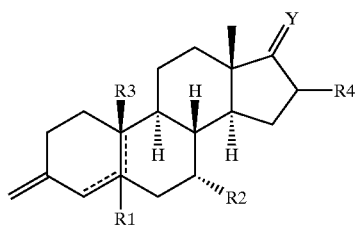

Formula 1 wherein
  $R^1$ is H or together with $R^3$ forms a β-epoxide or $R^1$ is absent if there is a 5–10 or 4–5 double bond;
  $R^2$ is $(C_1-C_5)$alkyl or $CF_3$;
  $R^3$ is βH, $βCH_3$ or together with $R^1$ forms a β-epoxide or $R^3$ is absent if there is a 5–10 double bond;
  $R^4$ is H, lower alkyl;
  Y is [H, H] [OH, H], =O, [OH, lower alkyl], [OH, $(C_2-C_5)$alkenyl], [OH, $(C_2-C_5)$alkynyl] or $(C_1-C_6)$ alkylidene, whereby said alkyl, alkenyl, alkynyl and alkylidene is optionally halogenated; or $=NOR^5$, whereby $R^5$ is H, lower alkyl.
  Dotted lines represent an optional double bond.

Preferred compounds according to the invention are those wherein $R^4$ is H and Y is [OH, H], =O, [OH, lower alkyl], [OH, $(C_2-C_5)$alkenyl], [OH, $(C_2-C_5)$alkynyl] or $(C_1-C_6)$ alkylidene, whereby said alkyl, alkenyl, alkynyl and alkylidene optionally might be halogenated.

In this description terms have the following meaning:

A lower alkyl is a branched or unbranched alkyl group having preferably 1–6 carbon atoms, like hexyl, isobutyl, tertiary butyl, propyl, isopropyl, ethyl, and methyl. Most preferred are alkyl groups having 1–3 carbon atoms.

$(C_1-C_5)$alkyl is a branched or unbranched alkyl group having 1–5 carbon atoms, for example methyl, ethyl, isopropyl, butyl, sec-butyl, tert-butyl etc.; Preferred are alkyl groups having 1–3 carbon atoms.

$(C_2-C_5)$alkenyl is a branched or unbranched alkenyl group having 2 to 5 carbon atoms, such as ethenyl, 2-butenyl, etc. Preferred are alkenyl groups having 2–3 carbon atoms.

$(C_2-C_5)$alkynyl is a branched or unbranched alkynyl group having 2–5 carbon atoms, such as ethynyl and propynyl etc. Preferred are alkynyl groups having 2–3 carbon atoms.

$(C_1-C_5)$alkylidene is a branched or unbranched alkylidene group having 1–5 carbon atoms, such as methenyl, butylidene etc. Preferred are alkylidene groups having 2–3 carbon atoms.

Halogen is fluorine, chlorine, bromine, and iodine.

Prodrugs are compounds which are designed to form a compound of the invention in the body of a recipient for treatment. In general such prodrugs can be esters or ethers of the 17-hydroxyl function.

A preferred embodiment of this invention is a compound as described above having a 5–10 double bond. Most preferred is the compound (7α,17α)-7-methyl-3-methylene-19-norpregn-5(10)-en-20-yn-17-ol. Excluded from the invention are the compounds (7α,17β)-7α-methyl-3-methylene-4-estren-17-ol, (7α,17α)-7-methyl-3-methylene-19-norpregn-4-ene-17-ol, (7α,17α)-7-methyl-3-methylene-19,21-dinorpregn-4-ene-17-ol, (7α)-17-keto-7-methyl-3-methylene-4-estrene, (7α,17α)-7-methyl-3-methylene-19-norpregn-4-en-20-yn-17-ol, 17β-hydroxy-7α-methyl-3-methylene-17α-propen-2-yl-4-estrene, and 17β-hydroxy-7α-methyl-3-methylene-17α-buten-2-yl-4-estrene. The disclaimer relates to the disclosures in BE 696,235.

The epoxide compounds ($R_1$ and $R_3$ together form β-O-) of this invention can be prepared by oxidation of a compound having the formula 2 in which the symbols have the meaning as defined above, with metachloroperoxybenzoic acid

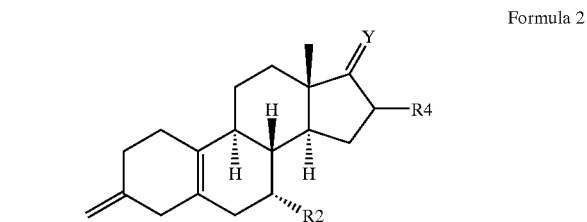

Formula 2

The 3-methylene group in a compound of the invention can be obtained by performing a Wittig reaction using methyltriphenylphosphonium bromide and potassium t-butoxide with corresponding 3-keto precursor steroids, which are characterized by formula 3, wherein $Y^2$ is as Y, as defined above, except that it is not =O and the other symbols have the meaning as defined before.

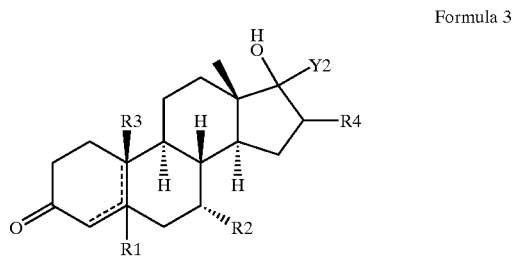

Formula 3

The 17-alkylidene compounds of the invention can be prepared by a Wittig reaction of a 3-ketal derivative of the 17-keto derivative according to formula 4, wherein the symbols have the meaning as defined before, with an alkyltriphenylphosphonium bromide followed by the hydrolysis of the 3-ketal function. The compounds having Y=H, H at the 17-position (formula 2) of the invention can be prepared by Wolff-Kishner reduction of the 17-keto moiety of the 3-ketal compound of formula 4, wherein the symbols have the meaning as defined before. The 17-oxime derivatives of the invention can be prepared by condensation of the 17-ketofunction (formula 4) with hydroxylamine derivatives. The 16-alkyl compound of the invention can be prepared by alkylation of the 16-position of the 17-keto compound (Y=O, formula 4).

Formula 4

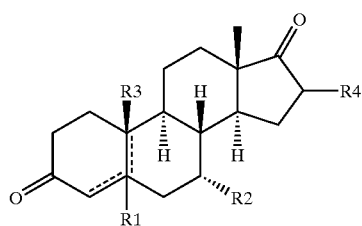

The above indicated reagents for transformation of the starting compounds and their ways of reacting with compounds are known in the art, but not yet applied for the group of compounds to be prepared to obtain the compounds of the invention. Starting materials can be obtained by methods described in the literature. A specifically relevant reference is Van Vliet et al. Recl.Trav.Chim.Pays-Bas; EN; 105; 4; 1986; 111–115, which text is incorporated into this description by way of reference. Notably, it is described therein that 17-alkyl-3-keto-derivatives according to formula 3, wherein $Y^2$ is [OH, lower alkyl] and the other symbols have the meaning as defined before, can be obtained by catalytic hydrogenation, for example with $PtO_2/H_2$, of a compound according to formula 3, wherein $Y^2$ is [OH, alkenyl] or [OH, alkynyl] and the other symbols have the meaning as defined before. Derivatives according to formula 5 can be obtained by purification from a mixture of compounds formed after the Birch reduction of the 4-en-3-one derivative according to formula 6, whereby both in formula 5 and in formula 6 the symbols have the meanings as defined before.

Formula 5

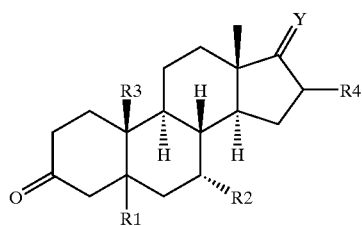

Formula 6

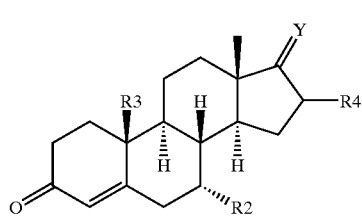

A 4-en-3-one derivative according to formula 6, wherein $R^3$ is H and the other symbols have the meanings as defined before, can be obtained from a compound according to formula 7 by double bond isomerisation (according to methods described in van Vliet et. al. 1986).

Formula 7

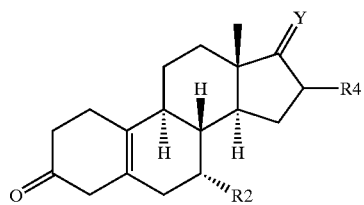

A 4-en-3-one derivative according to formula 6, wherein $R^3$ is methyl and the other symbols have the meanings as defined before, can be obtained according to the methods described in Grunwell et. al., Steroids Vol. 27, pages 759–771, 1976, which publication is incorporated herein by reference.

Further methods to obtain compounds according to formula 7 as starting material can be prepared as described by van Vliet et al. 1986.

The use of compounds as defined by formula 1 is for immunomodulation in mammals. A compound of this invention can in particular be used in the treatment of arthritic diseases such as rheumatoid arthritis (RA) and autoimmune diseases (AIDs) such as Sjögren's syndrome and systemic lupus erythematosus (SLE). It can also be used prophylactically for such diseases. Furthermore, a compound according to this invention can be used for the preparation of medicines comprising a compound of this invention as an active constituent.

The present invention also relates to a pharmaceutical composition comprising the steroid compound according to the invention, mixed with one or more pharmaceutically acceptable auxiliaries, such as described in the standard reference Gennaro et al., *Remmington's Pharmaceutical Sciences*, (18th ed., Mack publishing Company, 1990, see especially Part 8: Pharmaceutical Preparations and Their Manufacture.). A mixture of one or more of the steroid compounds according to the invention and one or more pharmaceutically acceptable auxiliaries may be compressed into solid dosage units, such as pills, tablets, or be processed into capsules or suppositories. By means of pharmaceutically suitable liquids the compounds can also be applied as an injection preparation in the form of a solution, suspension, emulsion, or as a spray, e.g. nasal spray. For making dosage units, e.g. tablets, the use of conventional additives such as fillers, colorants, polymeric binders and the like is contemplated. In general any pharmaceutically acceptable additive which does not interfere with the function of the active compounds can be used. The steroid compounds of the invention may also be included in an implant, a patch, a gel, and any other preparation for sustained release. Suitable carriers with which the compositions can be administered include lactose, starch, cellulose derivatives and the like, or mixtures thereof used in suitable amounts.

In another aspect, the invention relates to the use of the steroid compound according to the invention for the manufacture of a medicament for modulation of the immune system of a mammal. More specifically, the invention relates to the use of the steroid compound according to the invention for the manufacture of a medicament for the treatment of arthritic diseases such as rheumatoid arthritis (RA) and autoimmune diseases (AIDs) such as Sjögren's syndrome and systemic lupus erythematosus (SLE). Such medicaments can also be prepared for prophylactic use for such diseases. The medicament is preferably made suitable, in particular for the treatment of human beings by complying to the regulations of health authorities in diverse countries. The use of the 3-methylene steroid derivatives (7α,17β)-7α-methyl-3-methylene-4-estren-17-ol, (7α,17α)-7-methyl-3-methylene-19-norpregn-4-ene-17-ol, (7α,17α)-7-methyl-3-methylene-19,21-dinorpregn-4-ene-17-ol, (7α)-17-keto-7-methyl-3-methylene-4-estrene, (7α,17α)-7-methyl-3-methylene-19-norpregn-4-en-20-yn-17-ol, 17β-hydroxy-7α-methyl-3-methylene-17α-propen-2-yl-4-estrene, and 17β-hydroxy-7α-methyl-3-methylene-17α-buten-2-yl-4-estrene is within the ambit of the present invention.

Furthermore, the invention pertains to the treatment of arthritic diseases such as rheumatoid arthritis (RA) and autoimmune diseases (AIDs) such as Sjögren's syndrome and systemic lupus erythematosus (SLE), comprising the administration to a patient of a compound as described previously (in a suitable pharmaceutical dosage form). The dosage amounts of the present steroids will be of the range of from 0.001 to 100 mg per administration of a subject in need of treatment. Consequently dosage units for practical use of a compound of this invention can contain an amount of active ingredient in the range of from 0.001 to 100 mg.

The immuno-modulating properties of a compound of this invention can be demonstrated and used in the following procedures.

In the delayed type hypersensitivity (DTH) procedure, the effect of a compound on the development of an immune reaction can be observed in mice (details in example 16). Briefly, the compound is administered daily and the animals are immunized subsequently with an antigen in adjuvant. After 7 days the animals are challenged locally by injecting the antigen locally (mostly in the foot) and measuring the subsequently developing local swelling in response to the deposition of the antigen. The degree of this swelling is related to the development of an immune response against the eliciting antigen. The inhibiting action of a compound of this invention on the development of this swelling can be determined, by comparing the treatment group with a placebo treated group. As a reference treatment, administration of glucocorticoids can be used.

The effect of a compound of this invention was also tested in arthritic mice.

In this procedure, mice are immunized with collagen type 11, mostly from bovine cartilage, in an adjuvant. After three weeks a booster with the same antigen is given. Approximately 7–10 days after the booster reaction edema of the joints (especially in the hind and forefeet) can be observed. This swelling increases rapidly, leading to redness, inflammation and distortion of normal function. Upon X-ray analysis disruption of normal joint architecture can be observed. Upon histological examination of these joints, severe inflammation leading to disruption of normal cartilage architecture can be observed. The degree of observable alterations can be graded; moreover, the degree of histological alterations can be graded also.

Furthermore, the effect of a compound on this invention can be observed in non-obese diabetic (NOD)-mice.

In this procedure, mice spontaneously and gradually develop auto-immune diseases with symptoms resembling those of human insulin dependent diabetes mellitus (IDDM) and Sjögren's syndrome. Sjögren's syndrome is characterized by the development of infiltrates in the salivary and lachrymal gland. In NOD mice especially the salivary gland is characterized by the gradual development of infiltrates. A compound of this invention inhibits dose-dependently the development of these infiltrates in the submandibular glands.

IDDM is characterized by the development of infiltrates in the pancreas, leading to destruction of the islets of Langerhans producing insulin. After the gradual destruction of all these islets, no insulin production is present anymore resulting in the development of IDDM.

In the following examples the invention is illustrated.

EXAMPLE 1

Preparation of (7α,17α)-7-Methyl-3-methylene-19-norpregn-5(10-en-20-yn-17-ol

Methyltriphenylphosphonium bromide (26.4 g, 73.9 mmol) was added to a stirred solution of potassium t-butoxide (7.9 g, 70.4 mmol) in 130 ml dry THF under a nitrogen atmosphere. The yellow suspension was stirred for 45 minutes at room temperature. A solution of 20 g, 64 mmol tibolone in 200 ml dry THF was added rapidly (approx. 30 seconds) to the suspension, resulting in a slightly exothermic reaction (from 20° C. to 33° C.). The yellow reaction mixture was stirred for 30 minutes at room temperature, poured on ice-water (700 ml) and extracted with ethyl acetate (700 ml). The organic layer was washed with water (300 ml), dried ($Na_2SO_4$) and evaporated to dryness to give 41.8 g of a yellow oil. Column chromatography using toluene/ethyl acetate 95/5 (v/v %) as eluent gave 19.5 g of a colorless oil containing approximately 90% (7α,17α)-7-methyl-3-methylene-19-norpregn-5(10)-en-20-yn-17-ol and 10% the isomeric $\Delta^4$ derivative. Recrystallization (3 times) using heptane/petroleum ether as solvent gave the title compound (6.44 g, yield 32%) as a white solid, mp 91.6° C.

EXAMPLE 2

Preparation of (7α,17β)-7-Methyl-3-methyleneestr-5(10)-en-17-ol

Methyltriphenylphosphonium bromide (4.21 g, 11.8 mmol) was added to a stirred solution of potassium t-butoxide (1.26 g, 11.2 mmol) in 20 ml dry THF under a nitrogen atmosphere. The yellow suspension was stirred for 45 minutes at room temperature. A solution of (7α,17β)-7-methyl-3-keto-estr-5(10)-en-17-ol (3.4 g, 11.8 mmol) in 25 ml dry THF was added rapidly to the suspension. The yellow reaction mixture was stirred for 30 minutes at room temperature, poured on ice-water and extracted with ethyl acetate. The organic layer was washed with water, dried ($Na_2SO_4$) and evaporated to dryness to give 5.3 g of the title compound as a yellow oil. Column chromatography using toluene/ethyl acetate 95/5 (v/v %) as eluent gave 2.3 g of a colorless oil. Crystallization using heptane/petroleum ether gave (7α,17β)-7-methyl-3-methyleneestr-5(10)-en-17-ol (1.47 g, 44%) as a white solid, mp 111.8° C.

EXAMPLE 3

Preparation of (5β,7α,17α-5,10-Epoxy-7-methyl-3-methylene-19-norpregn-20-yn-17-ol The compound (7α,17α)-7-methyl-3-methylene-19-norpregn-5(10)-en-20-yn-17-ol (390 mg, 1.26 mmol) obtained according to example 1 was stirred in 15 ml dry dichloromethane under a nitrogen atmosphere. The solution was cooled to 0° C. and meta-chloroperoxybenzoic acid (1.26 mmol, 310 mg 70% mcpba) was added. The reaction mixture was stirred for 2 hours at 0° C., washed with a saturated sodium thiosulfate solution, saturated sodium bicarbonate solution and a saturated sodium chloride solution, dried ($Na_2SO_4$) and evaporated to dryness to give 450 mg crude (5β,7α,17α)-5,10-epoxy-7-methyl-3-methylene-19-norpregn-20-yn-17-ol. Column chromatography using heptane/ethyl acetate 95/5 (v/v %) as eluent gave the purified title compound (150 mg, 37%) as foam.

EXAMPLE 4

Preparation of (5β,7α,17β)-5,10-Epoxy-7-methyl-3-methyleneestran-17-ol

Compound (7α,17p)-7-methyl-3-methyleneestr-5(10)-en-17-ol (350 mg, 1.22 mmol), obtained according to example 2, was stirred in 15 ml dry dichloro methane under a nitrogen atmosphere. The solution was cooled to 0° C. then meta-chloroperoxybenzoic acid (1.22 mmol, 301 mg 70% mcpba) was added. The reaction mixture was stirred for 75 minutes at 0° C., washed with a saturated sodium thiosulfate solution, saturated sodium bicarbonate solution and a saturated sodium chloride solution, dried ($Na_2SO_4$) and evaporated to dryness to give 370 mg crude (5β,7α,17β)-5,10-epoxy-7-methyl-3-methyleneestran-17-ol. Column chromatography using heptane/ethyl acetate 95/5 (v/v %) as eluent gave further purified title compound (230 mg, 63%). Crystallization using heptane/ethyl acetate 95/5 (v/v%) gave the purified title compound (120 mg, 33%) as a white solid, mp 125° C.

EXAMPLE 5

Preparation of (5α,7α,17α)-7-Methyl-3-methylene-19-norpregn-20-en-17-ol

Methyltriphenylphosphonium bromide (688 mg, 1.93 mmol) was added to a stirred solution of potassium t-butoxide (196 mg, 1.75 mmol) in 2 ml dry THF under a nitrogen atmosphere. The yellow suspension was stirred for 45 minutes at room temperature. A solution of (5α,7α,17α)-7-methyl-3-keto-19-norpregn-20-en-17-ol (220 mg, 0.7 mmol) in 3 ml dry THF was added rapidly to the suspension. The yellow reaction mixture was stirred for 2.5 hours at room temperature, poured on ice-water and extracted with ethyl acetate. The organic layer was washed with water, dried ($Na_2SO_4$) and evaporated to dryness to give 500 mg of an oil. Column chromatography using toluene/ethyl acetate 95/5 (v/v %) as eluent gave 200 mg crude (5α,7α,17α)-7-methyl-3-methylene-19-norpregn-20-en-17-ol. Crystallization from heptane gave the purified title compound (120 mg, 55%) as a white solid, mp 105° C.

EXAMPLE 6

Preparation of (5α,7α, 17α)-7-Methyl-3-methylene-19-norpregn-20-yn-17-ol

Methyltriphenylphosphonium bromide (1.85 g, 5.18 mmol) was added to a stirred solution of potassium t-butoxide (527 mg, 4.7 mmol) in 4 ml dry THF under a nitrogen atmosphere. The yellow suspension was stirred for 45 minutes at room temperature. A solution of (5α,7α,17α)-7-methyl-3-keto-19-norpregn-20-yn-17-ol (590 mg, 1.88 mmol) in 8 ml dry THF was added rapidly to the suspension. The yellow reaction mixture was stirred for 2.5 hours at room temperature, poured on ice-water and extracted with ethyl acetate. The organic layer was washed with water, dried ($Na_2SO_4$) and evaporated to dryness to give 1.8 g of an oil. Column chromatography using toluene/ethyl acetate 95/5 (v/v %) as eluent gave 590 mg crude (5α,7α,17α)-7-methyl-3-methylene-19-norpregn-20-yn-17-ol. Crystallization from heptane gave purified title compound (290 mg, 50%) as a white solid, mp 97° C.

EXAMPLE 7

Preparation of (5β,7α,17α)-7-Methyl-3-methylene-19-norpregnan-17-ol

Methyltriphenylphosphonium bromide (5.4 g, 15.1 mmol) was added to a stirred solution of potassium t-butoxide (1.62 g, 14.4 mmol) in 27 ml dry THF under a nitrogen atmosphere. The yellow suspension was stirred for 40 minutes at room temperature. A solution of (5β,7α,17α)-7-methyl-3-keto-19-norpregnan-17-ol (4.56 g, 14.4 mmol) in 50 ml dry THF was added rapidly to the suspension. The yellow reaction mixture was stirred for 30 minutes at room temperature, poured on ice-water and extracted with ethylacetate. The organic layer was washed with water and brine, dried ($Na_2SO_4$) and evaporated to dryness to give 8.2 g of an oil. Column chromatography using toluene/ethyl acetate 95/5 (v/v %) as eluent gave (5β,7α,17α)-7-methyl-3-methylene-19-10 norpregnan-17-ol (3.65 g, 81%) which solidified upon standing, mp 104° C.

EXAMPLE 8

Preparation of (7α)-7-Methyl-3,17-dimethyleneestr-5(10)ene

Methyltriphenylphosphonium bromide (2.2 g, 6 mmol) was added to a stirred solution of potassium t-butoxide (680 mg, 6 mmol) in 25 ml dry THF under a nitrogen atmosphere. The yellow suspension was stirred for 30 minutes at room temperature. A solution of (7α)-7-methyl-3-keto-17-methyleneestr-5(10)ene (850 mg, 3 mmol) in 25 ml dry THF was added rapidly (approx. 30 seconds) to the suspension, resulting in a slightly exothermic reaction. The reaction mixture was stirred for 30 minutes at room temperature, poured on ice-water (100 ml) and extracted with ethyl acetate (100 ml). The organic layer was washed with water (50 ml), dried ($Na_2SO_4$) and evaporated to dryness to give (7α)-7-methyl-3,17-dimethyleneestr-5(10)ene (680 mg, 80%) as a colorless oil. $[\alpha]_D$ +115° (c 0.185 in ethanol).

EXAMPLE 9

Preparation of (7α,16α,17β)-7,16-Dimethyl-3-methylene-17-(1-propynyl)estr-5(10)-en-17-ol A solution of (7α)-3,3-dimethoxy-7-methylestr-5(10)-en-17-one (1.5 g, 4.5 mmol) and 1,3-dimethyl-3,4,5,6-tetrahydro-2(1H)-pyrimidinone (DMPU, 1.2 mL, 9.9 mmol) in 30 mL dist. THF was added in approx. 8 minutes to a stirred solution of lithium bis(trimethylsilyl)amide (LiHMDS, 4.96 mL, 1M in THF) in 15 mL distillated THF at −40° C. under a nitrogen atmosphere. The reaction mixture was stirred for 45 minutes at −40° C. A solution of iodomethane (730 μL, 11.7 mmol) in 1 mL dist. THF was added and stirred for 1 hour and the temperature was allowed to warm up to 0° C. Water and sat. ammonium chloride solution were added and extracted with ethyl acetate. The organic layer was washed with brine, dried ($Na_2SO_4$) and evaporated to dryness. Column Chromatography using heptane/ethyl acetate 95/5 (v/v %) as eluent gave (7α,16α)-3,3-dimethoxy-7,16-dimethylestr-5(10)-en-17-one (990 mg, yield 65%).

Propyn (approx. 4 g, 100 mmol) was bubbled through a solution of n-BuLi (9 mL, 1.6M in hexane) in 19 mL dry THF at −70° C. to give an exothermic reaction (from −70° C. to −30° C.). A solution of (7α,16α)-3,3-dimethoxy-7,16-dimethylestr-5(10)-en-17-one (990 mg, 2.86 mmol) in 10 mL dry THF was added in approx. 5 minutes to the white suspension under a nitrogen atmosphere. The reaction mixture was stirred for 45 minutes and the temperature was allowed to warm up slowly to room temperature. Water and sat. ammonium chloride solution were added and extracted with ethyl acetate. The organic layer was washed with brine, dried ($Na_2SO_4$) and evaporated to dryness to give (7α,16α,17β)-3,3-dimethoxy-7,16-dimethyl-17-(1-propynyl)estr-5(10)-en-17-ol. A solution of oxalic acid (72 mg, 0.57 mmol) in 6 mL water was added to the solution of (7α,16α,17β)-3,3-dimethoxy-7,16-dimethyl-17-(1-propynyl)estr-5(10)-en-17-ol (2.86 mmol) in 25 mL ethanol and the reaction mixture was stirred for 45 minutes at room temperature. A solution of saturated sodium hydrogen carbonate was added and extracted with ethyl acetate. The organic layer was washed with brine, dried ($Na_2SO_4$) and evaporated to dryness. Column Chromatography using heptane/ethyl acetate 9/1 (v/v %) as eluent gave 7α, (16α-17β)-7,16-dimethyl-17-hydroxy-17-(1-propynyl)estr-5(10)-en-3-one (940 mg, yield 97%).

Methyltriphenylphosponium bromide (1.7 g, 4.7 mmol) was added to a suspension of potassium tert-butoxide (470 mg, 4.2 mmol) in 31 mL dry toluene under a nitrogen atmosphere. The reaction mixture was stirred for 45 minutes at reflux temperature. The reaction mixture was cooled to 4° C. and a solution of (7α,16α-17β)-7,16-dimethyl-17-hydroxy-17-(1-propynyl)estr-5(10)-en-3-one (940 mg, 2.76 mmol) in 39 mL dry toluene was added in approx. 10 minutes. The reaction mixture was stirred for 20 minutes at 4° C. and diluted sodium chloride was added and extracted with ethyl acetate. The organic layer was washed with brine, dried ($Na_2SO_4$) and evaporated to dryness. Column Chromatography using heptane/ethyl acetate 95/5 (v/v %) as eluent gave (7α,16α,17β)-7,16-dimethyl-3-methylene-17-(1-propynyl)estr-5(10)-en-17-ol (630 mg, yield 67%) as oil. The product was freeze-dried from dioxane. $[α]_D$ +83° (c 0.15 in ethanol).

EXAMPLE 10

Synthesis of (7α,16α,17β)-16-Ethyl-7-methyl-3-methylene-17-(1-propynyl)estr-5(10)-en-17-ol This compound was prepared according to the methods described above starting from (7α)-3,3-dimethoxy-7-methylestr-5(10)-en-17-one and ethyliodide, $[α]_D$ +54° (c 0.13 in ethanol).

EXAMPLE 11

Synthesis of (7α,17β)-7-Methyl-3-methylene-17-(1-propynyl)estr-5(10)-en-17-ol

This compound was prepared according to the methods described above starting from (7α)-3,3-dimethoxy-7-methylestr-5(10)-en-17-one.

$[α]_D$ +80° (c 0.14 in ethanol).

EXAMPLE 12

Synthesis of (7α,16β,17β)-16-Ethyl-7-methyl-3-methylene-19-norpregn-5(10)-en-20-yn-17-ol This compound was prepared according to the synthesis described above starting from (7α)-3,3-dimethoxy-7-methylestr-5(10)-en-17-one, $[α]_D$ +94° (c 0.10 in ethanol).

EXAMPLE 13

Preparation of (7α)-3-Methylene-7-methylestr-5(10)-ene

Potassium hydroxide (1.5 g, 27 mmol) and hydrazine monohydrate (3 ml, 62 mmol) were added to a suspension of (7α)-3,3-dimethoxy-7-methylestr-5(10)-en-17-one (1 g, 3 mmol) in 17 mL diethyleneglycol at room temperature under a nitrogen atmosphere. The reaction mixture was heated for 1 hour at 130° C. followed by 1 hour and 15 minutes at 230° C. A Dean-Stark trap was used to remove the water and the excess of hydrazine. The reaction mixture was cooled down to room temperature and water was added and extracted with ethyl acetate. The organic layer was washed with brine, dried ($Na_2SO_4$) and evaporated to dryness to give the crude product (7α)-3,3-dimethoxy-7-methylestr-5(10)-ene, which was converted into (7α,16α,17β)-7,16-dimethyl-3-methylene-17-(1-propynyl)estr-5(10)-en-17-ol according to the procedures described above, mp 57° C.

EXAMPLE 14

Synthesis of (7α)-3-Methylene-7-methylestr-5(101-en-17-one O-methyloxime (7α)-3,3-Dimethoxy-7-methylestr-5(10)-en-17-one (100 mg, 0.3 mmol) was added to a solution of methoxylamine. HCl (100 mg, 1.2 mmol) and sodium acetate (123 mg, 1.5 mmol) in 6 mL MeOH. The reaction mixture was stirred for 3 days at room temperature. Water and a solution of saturated sodium hydrogen carbonate was added and extracted with ethyl acetate. The organic layer was washed with brine, dried ($Na_2SO_4$) and evaporated to dryness to give the crude (7α)-3,3-dimethoxy-7-methylestr-5(10)-en-17-one O-methyloxime, which was converted into (7α)-3-methylene-7-methylestr-5(10)-en-17-one O-methyloxime according to the methods described above, $[α]_D$ +149° (c 0.11 in ethanol).

EXAMPLE 15

Synthesis of (7α)-3-Methylene-7-methylestr-5(10)-en-17-one oxime

This oxime was prepared from (7α)-3,3-Dimethoxy-7-methylestr-5(10)-en-17-one and hydroxylamine.HCl according to the methods described above, mp 149° C.

EXAMPLE 16

Delayed Type Hypersensitivity (DTH) Reaction

Groups of eight female Balb/c (Harlan, Zeist, The Netherlands) mice were used, approximately 8 weeks of age at the start of the experiment. These mice were housed in Macrolon cages, under standard conditions and acclimatized for 3–5 days before the start of the experiment. The groups received either compound or placebo.

They were weighed on day 1 and on the last treatment day. Animals were treated once daily by subcutaneous (sc) injection in the back of the neck or by oral gavage from day 1 till day 11 with a test compound in concentration range from 1.2, 3, 4, 6, to 12 mg/kg. The injection volume was 0.1 mL of a vehicle for injection consisting of physiological saline containing 0.5% gelatin and 5% mannitol. A placebo treated group (vehicle only) and a group treated with 4 mg/kg dexamethasone as reference compound were included in each experiment.

On day 2, animals were immunized with 0.1 ml of a stable suspension of 3.75 Lf Tetanus Toxoid antigen (TT from the RIVM, Zeist, The Netherlands) in 1 mg/ml dimethyl dioctadecylammonium bromide (DDA) from Phase Sep, at 2 places on the breast intradermally.

On day 9 animals were challenged on the ventral side of the right [R] paw with 0.05 mL of a solution containing 50 Lf TT and 1 mg Al(OH)$_3$ per mL. The left [L] footpad (control) received the vehiculum with Al(OH)$_3$ only. After 24 and 48 hours, the left and right footpad thickness (parameters L and R, respectively) were measured with a calipers densitometer in mm and the percentage of antigen-specific footpad swelling was calculated according to the formula: [(R−L)/L]×100%. Results

| Compound | Amount of compound given sc. in mg/kg leading to 50% reduction of the DTH reaction as compared to placebo |
|---|---|
| example 1 | 1.9–3.4 |
| example 2 | 20 |
| example 3 | 11 |
| example 4 | >20 |
| example 5 | 10 |
| example 7 | 6 |

EXAMPLE 17
Non-obese Diabetic (NOD)-mice

NOD mice used, were either bred in house (breeding pairs originally obtained from Hattori, Boston, USA, at generation 58) or obtained from Bomholtgård (Denmark) at 6–7 weeks of age.

Only female mice were used for assessing effects of compounds on spontaneous sialoadenitis development, as characterized by leucocyte infiltrations in submandibular glands.

Groups of 6–8 female mice were housed under standard conditions and treated once daily (either sc. or orally) from week 8 till 14 or 20 weeks of age with 0.1 ml of compound (concentration 1.2, 4, or 12 mg/kg/day) or placebo (vehicle only) or were not treated. From week 12 onwards they were tested weekly for the presence of urinary glucose (Diabur-test 5000, Boehringer Mannheim).

At week 8 (pre-treatment-group) or at week 14 or 20, after respectively 6 or 12 weeks of treatment, animals were killed under ether anesthesia; organs were removed, dissected free of fat and weighed. Submandibular glands were fixed in sublimate-formol for 18–24 hours and transferred to alcohol 70%. Tissue sections were embedded in paraffin and HE stained according to standards methods. Scoring of tissue sections for infiltrates was microscopically performed by two independent observers according to standard methods. Activity of compounds of this invention can be demonstrated in this test.

EXAMPLE 18
Collagen Arthritis

Female DBA-1J/BOM mice were purchased from Bomholtgård, Denmark. All animals were housed under standard conditions and acclimatized for at least 7 days.

At the age of 10–12 weeks all animals were immunized intradermally at the base of the tail with 100 μg of an emulsion of purified bovine collagen type II [CII] (2 mg/mL in 0.05 acetic acid) emulsified in equal volumes of Complete Freund's Adjuvant (CFA, containing 4 mg/mL MT H37Ra, Difco Laboratories, Detroit, USA). At 21 days after immunization, a booster injection was administered intraperitoneally of 100 μg CII dissolved in saline. Treatment was given once daily starting at day 1 (day before immunization) until autopsy at day 44.

Groups consisting of 9 to 10 animals were treated either with test compound (1.5 mg/kg/day daily until day 22, from that day on reduced to 3 times a week), or cyclosporin A (100 mg/kg/day initially, from day 4, 20 mg/kg), or dexamethasone (2 mg/kg/day), or vehicle (5% Mulgofen(EL 719, GAF) in saline). A non-treated control group was included.

Mice were weighed every week, and clinical arthritis activity (visual appearance of arthritis in peripheral joints) was scored (according to standard methods) by one observer not aware of the treatment given, from day 19 onward every 2–3 days, until autopsy at day 44.

Clinical arthritis was graded on a scale of 0–2 per paw and expressed as a cumulative arthritis score per mouse with a maximum score of 8. At the end of the experiment knee and ankle joints were isolated and used for X-ray analysis as a marker for bone destruction, followed by immediate fixation in 4% formaldehyde for histology.

X-ray photographs were carefully examined using a stereo microscope and bone destruction of joints was scored on a scale of 0–5 according to standard methods/ranging from undamaged to complete destruction. Activity of compounds of this invention can be demonstrated in this test.

What is claimed is:

1. A 3-methylene steroid derivative having the general formula 1

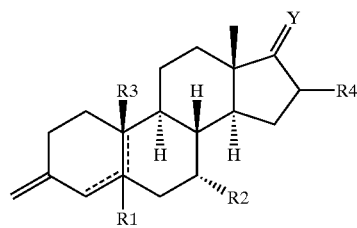

Formula 1 wherein

R1 is H or together with R3 forms a β-epoxide or R1 is absent if there is a 5–10 or 4–5 double bond;

R2 is (C1–C5)alkyl or CF3;

R3 is βH, βCH3 or together with R1 forms a β-epoxide or R3 is absent if there is a 5–10 double bond;

R4 is H, or lower alkyl;

Y is [H, H] [OH, H], =O, [OH, lower alkyl], [OH, (C2–C5)alkenyl], [OH, (C2–C5)alkynyl] or (C1–C6) alkylidene, wherein said alkyl, alkenyl, alkynyl or alkylidene is optionally halogenated; or =NOR5, wherein R5 is H[,] or lower alkyl;

dotted lines represent an optional double bond; or a salt, solvate or prodrug thereof, with the proviso that the 3-methylene steroid derivative is not (7α,17β)-7α-methyl-3-methylene-4-estren-17-ol, (7α, 17α)-7-methyl-3-methylene-19-norpregn-4-ene-17-ol, (7α, 17α)-7-methyl-3-methylene-19,21-dinorpregn-4-ene-17-ol, (7α)-17-keto-7-methyl-3-methylene-4-estrene, (7α,17α)-7-methyl-3-methylene-19-norpregn-4-en-20-yn-17-ol, 17β-hydroxy-7α-methyl-3-methylene-17α-propen-2-yl-4-estrene, or 17β-hydroxy-7α-methyl-3-methylene-17α-buten-2-yl-4-estrene.

2. The 3-methylene steroid derivative according to claim 1, wherein the 3-methylene steroid derivative has a 5–10 double bond and R1 and R3 are absent.

3. A 3-methylene steroid derivative (7α,17α)-7-methyl-3-methylene-19-norpregn-5(10)-en-20-yn-17-ol.

4. A pharmaceutical composition, comprising:
a 3-methylene steroid derivative according to claim 1 or a pharmaceutically acceptable salt or solvate thereof, in admixture with a pharmaceutically acceptable auxiliary.

5. A method for treating arthritic diseases or autoimmune diseases, comprising:

administering an effective amount of a 3-methylene steroid derivative having the general formula 1

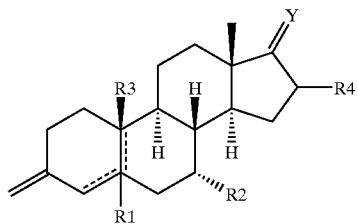

Formula 1 wherein

R1 is H or together with R3 forms a β-epoxide or R1 is absent if there is a 5–10 or 4–5 double bond;

R2 is (C1–C5)alkyl or CF3;

R3 is βH, βCH3 or together with R1 forms a β-epoxide or R3 is absent if there is a 5–10 double bond;

R4 is H, or lower alkyl;

Y is [H, H] [OH, H], =O, [OH, lower alkyl], [OH, (C2–C5)alkenyl], [OH, (C2–C5)alkynyl] or (C1–C6)alkylidene, wherein said alkyl, alkenyl, alkynyl or alkylidene is optionally halogenated; or =NOR5, wherein R5 is H, or lower alkyl;

dotted lines represent an optional double bond; or a pharmaceutically acceptable salt, solvate or prodrug thereof.

* * * * *

UNITED STATES PATENT AND TRADEMARK OFFICE
CERTIFICATE OF CORRECTION

PATENT NO.   : 6,579,864 B1
DATED        : June 17, 2003
INVENTOR(S)  : Ralf Plate and Willhelmina Maria Bagchus It is certified that error appears in the above-identified patent and that said Letters Patent is hereby corrected as shown below:

Column 2,
Lines 29-31, change compound from "17β-hydroxy-7α-methyl-3-methylene-17α-propen-2-yl-4-estrene, and 17β-hydroxy-7α-methyl-3-methylene-17α-buten-2-yl-4-estrene" to -- 17β-hydroxy-7α-methyl-3-methylene-17α-(2-propenyl) -4-estrene and 17β-hydroxy-7α-methyl-3-methylene-17α-(2-methyl-2-propenyl) -4-estrene --.

Column 5,
Lines 14-16, change compound from "17β-hydroxy-7α-methyl-3-methylene-17α-propen-2-yl-4-estrene, and 17β-hydroxy-7α-methyl-3-methylene-7α-buten-2-yl-4-estrene" to -- 17β-hydroxy-7α-methyl-3-methylene-17α- (2-propenyl) -4-estrene and 17β-hydroxy-7α-methyl-3-methylene-17α- (2-methyl-2-propenyl) -4-estrene --.

Column 12,
Lines 54-57, change compounds from "17β-hydroxy-7α-methyl-3-methylene-17α-propen-2-yl-4-estrene, and 17β-hydroxy-7α-methyl-3-methylene-17α-buten-2-yl-4-estrene" to -- 17β-hydroxy-7α-methyl-3-methylene-17α- (2-propenyl) -4-estrene and 17β-hydroxy-7α-methyl-3-methylene-17α- (2-methyl-2-propenyl) -4-estrene --.

Signed and Sealed this

Twenty-first Day of September, 2004

JON W. DUDAS
*Director of the United States Patent and Trademark Office*